US008318691B2

(12) United States Patent
Weichselbaum et al.

(10) Patent No.: US 8,318,691 B2
(45) Date of Patent: Nov. 27, 2012

(54) TREATMENT OF TUMORS WITH GENETICALLY ENGINEERED HERPES VIRUS

(75) Inventors: Ralph R. Weichselbaum, Chicago, IL (US); Bernard Roizman, Chicago, IL (US); Richard J. Whitley, Birmingham, AL (US)

(73) Assignees: Arch Development Corporation, Chicago, IL (US); UAB Research Foundation, Birmingham, AL (US)

( * ) Notice: Subject to any disclaimer, the term of this patent is extended or adjusted under 35 U.S.C. 154(b) by 131 days.

(21) Appl. No.: 12/802,443

(22) Filed: Jun. 7, 2010

(65) Prior Publication Data
US 2011/0002890 A1    Jan. 6, 2011

Related U.S. Application Data

(63) Continuation of application No. 09/964,042, filed on Sep. 26, 2001, now abandoned, which is a continuation of application No. 09/629,021, filed on Jul. 31, 2000, now abandoned.

(51) Int. Cl.
A61K 48/00    (2006.01)
(52) U.S. Cl. .................................................. 514/44 A
(58) Field of Classification Search .................. 514/44 A
See application file for complete search history.

(56) References Cited

U.S. PATENT DOCUMENTS

| 4,769,331 A | 9/1988 | Roizman et al. |
| 4,859,587 A | 8/1989 | Roizman |
| 4,999,296 A | 3/1991 | Kit et al. |
| 5,068,192 A | 11/1991 | Cochran et al. |
| 5,288,641 A | 2/1994 | Roizman |
| 5,328,688 A | 7/1994 | Roizman |
| 5,360,893 A | 11/1994 | Owens et al. |
| 5,585,096 A | 12/1996 | Martuza et al. |
| 5,593,879 A | 1/1997 | Steller et al. |

FOREIGN PATENT DOCUMENTS

| EP | 243155 | 10/1987 |
| EP | 453242 | 10/1991 |
| WO | WO-92/04050 | 3/1992 |
| WO | WO-96/00007 | 1/1996 |
| WO | WO-97/26904 | 7/1997 |

OTHER PUBLICATIONS

Aas et al., "Specific P53 mutations are associated with de novo resistance to doxorubicin in breast cancer patients," Nature Medicine, 2(7): 811-814 (1996).
Ackermann et al., "Characterization of Herpes Simplex Virus 1 α Proteins 0, 4, and 27 with Monoclonal Antibodies," J. Virology, 52(1):108-118 (1984).
Ackermann et al., "Identification by Antibody to a Synthetic Peptide of a Protein Specified by a Diploid Gene Located in the Terminal Repeats of the L Component of Herpes Simplex Virus Genome", J. Virol., 58(3):843-850 (1986).
Advani et al. "Enhanced Replication of Attenuated HSV-1 in Irradiated Human Glioma Xenografts" Intl. J. Rad. Oncol. Biol. Phys. 1997 vol. 39 pp. 251.
Advani, et al., "Replication-competent, Nonneuroinvasive Genetically Engineered Herpes Virus Is Highly Effective in the Treatment of Therapy-resistant Experimental Human Tumors1," Cancer Research 59:2055-2058 (1999).
Advani, S.J. et al. "Enhancement of Replication of Genetically Engineered Herpes Simplex Viruses by Ionizing Radiation: A New Paradigm for Destruction of Therapeutically Intractable Tumors," Gene Therapy, 5:160-165 1998.
Andreansky et al., "Evaluation of Genetically Engineered Herpes Simplex Viruses as Oncolytic Agents for Human Malignant Brain Tumors," Cancer Research, 57:1502-1509 (1997).
Andreansky et al., "Treatment of intracranial gliomas in immunocompetent mice using herpes simplex viruses that express murine interleukins," Gene Therapy, 5(1):121-130 (1998).
Barinaga, M., "Cell Suicide: By ICE, Not Fire", Science, 263:754-756 (1994).
Batistatou, A. et al., "Aurintricarboxylic Acid Rescues PC12 Cells and Sympathetic Neurons from Cell Death Caused by Nerve Growth Factor Deprivation: Correlation with Suppression of Endonuclease Activity", J. Cell Biol., 115(2):461-471 (1991).
Bischoff, J.R. et al., "An Adenovirus Mutant That Replicates Selectively in p53-Deficient Human Tumor Cells," Science, 274: 373-376 (Oct. 1996).
Braun et al., "Application of Denatured, Electrophoretically Separated, and Immobilized Lysates of Herpes Simplex Virus-Infected Cells for Detection of Monoclonal Antibodies and for Studies of the Properties of Viral Proteins," J. Virol., 46:103-112 (1983).
Brown et al., "Genetic Studies with Herpes Simplex Virus Type 1. The Isolation of Temperature-sensitive Mutants, their Arrangement into Complementation Groups and Recombination Analysis Leading to a Linkage Map," J. Gen. Virol., 18:329-346 (1973).
Brown, D. "Gene Therapy 'Oversold' By Researchers, Journalists", The Washington Post, A22, Friday, Dec. 8, 1995.
Carpenter, et al., "Sequences of the bovine herpesvirus 1 homologue of herpes simplex virus type-1 α-trans-inducing factor (UL48)," GENE 119:259-263 (1992).
Carroll et al. "Enhancement of gene therapy specificity for diffuse colon carcinoma liver metastases with recombinant herpes simplex virus" Ann Surg. Sep. 1996;224(3):323-9; discussion 329-30.
Centifanto-Fitzgerald et al., "Ocular Disease Pattern Induced by Herpes Simplex Virus is Genetically Determined by a Specific Region of Viral DNA", J. Exp. Med., 155:475-489 (1982).
Chambers et al., "Comparison of genetically engineered herpes simplex viruses for the treatment of brain tumors in a scid mouse model of human malignant glioma", Proc. Natl. Acad. Sci., USA, 92:1411-1415 (1995).
Chou and Roizman, "Herpes Simplex Virus 1 (HSV-1) Gene γ134.5 Blocks the Neuroblastoma Cells from Cell Death (Apoptosis) Induced by Viral Infection," J. Cell. Biochem., Keystone Symposia, Supplement 10C, Feb. 21-Mar. 7, 1992, Abstract N303, p. 136.

(Continued)

Primary Examiner — J. E. Angell
(74) Attorney, Agent, or Firm — Marshall, Gerstein & Borun LLP

(57) ABSTRACT

Disclosed are methods for treating cancer by administering an effective amount of a modified Herpes simplex virus.

16 Claims, No Drawings

OTHER PUBLICATIONS

Chou et al., "Association of a Mr 90,000 phosphoprotein with protein kinase PKR in cells exhibiting enhanced phosphorylation of translation initiation factor eIF-2α and premature shutoff of protein synthesis after infection with γ1 34.5-mutants of herpes simplex virus 1," Proc. Natl. Acad. Sci. (USA) 92:10516-10520 (1995).

Chou et al., "Isomerization of Herpes Simplex Virus 1 Genome: Identification of the cis-Acting and Recombination Sites within the Domain of the a Sequence", Cell, 41:803-811 (1985).

Chou et al., "The γ1 34.5 gene of herpes simplex virus 1 precludes neuroblastoma cells form triggering total shutoff of protein synthesis characteristic of programmed cell death in neuronal cells," Proc. Natl. Acad. Sci. (USA) 89:3266-3270 (1992).

Chou et al., "The Herpes Simplex Virus 1 Gene for ICP34.5, Which Maps in Inverted Repeats, Is Conserved in Several Limited-Passage Isolates but Not in Strain 17syn+", J. Virol., 64(3):1014-1020 (1990).

Chou et al., "The Terminal α Sequence of the Herpes Simplex Virus Genome Contains the Promoter of a Gene Located in the Repeat Sequences of the L Component", J. Virol., 57(2):629-637 (1986).

Chou, J. et al., "Mapping of Herpes Simplex Virus-1 Neurovirulence to γ134.5, a Gene Nonessential for Growth in Culture," Science, 250:1262-1266 (Nov. 1990).

Clem et al., "Prevention of Apoptosis by a Baculovirus Gene During Infection of Insect Cells," Science, 254:1388-1399 1991.

Coghlan, A., "Gene dream fades away", New Scientist, pp. 14-15 (Nov. 1995).

Corey et al., "Infections with Herpes Simplex Viruses," New England J. Medicine, 314:686-691 (1986).

Crystal, "Transfer of genes to humans: early lessons and obstacles to success" Science. Oct. 20, 1995;270(5235):404-10.

Culver, K.W. et al., "In Vivo Gene Transfer with Retroviral Vector-Producer Cells for Treatment of Experimental Brain Tumors," Science, 256:1550-1552 (Jun. 1992).

Datta et al., "Overexpression of Bcl-xL by Cytotoxic Drug Exposure Confers Resistance to Ionizing Radiation-induced Internucleosomal DNA Fragmentation," Cell Growth & Differentiation, 6:363-370 (Apr. 1995).

Davidson et al., "Location and Orientation of Homologous Sequences in the Genomes of Five Herpes Viruses," J. Gen. Virol., 64:1972-1942 (1983).

Deiss et al., "Functional Domains within the a Sequence Involved in the Cleavage-Packaging of Herpes Simplex Virus DNA", J. Virol., 59:605-618 (1986).

DeLuca et al., "Isolation and Characterization of Deletion Mutants of Herpes Simplex Virus Type 1 in the Gene Encoding Immediate-Early Regulatory Protein ICP4," J. Virology, 56(2):558-570 (1985).

Dolan et al., "Status of the ICP34.5 gene in herpes simplex virus type 1 strain 17," Journal General Virology. , 73 4 :971-973 1992.

Ejercito et al., "Characterization of Herpes Simplex Virus Strains Differing in their Effects on Social Behaviour of Infected Cells", J. Gen. Virol., 2:357-364 (1968).

Field et al., "The pathogenicity of thymidine kinase-deficient mutants of herpes simplex virus in mice", J. Hyg., Camb., 81:267-277 (1978).

Gagliardini et al., "Prevention of Vertebrate Neuronal Death by the crmA Gene", Science, 263:826-828 (1994).

Gregory et al., "Activation of Epstein-Barr Virus Latent Genes Protects Human B Cells From Death by Apoptosis," Nature, 349:612-614 (1991).

Gura, "Systems for Identifying New Drugs," Science 278:1041-1042 (1997).

Hallahan, et al. "Spatial and temporal control of gene therapy using ionizing radiation," Nature Medicine, 1(8):786-791 (1995).

Hammer et al., "Temporal Cluster of Herpes Simplex Encephalitis: Investigation by Restriction Endonuclease Cleavage of Viral DNA", J. Infectious Diseases, 141 4 :436-440(1980).

Hayward et al., "Anatomy of herpes simplex virus DNA: Evidence for four populations of molecules that differ in the relative orientations of their long and short components", Proc. Natl. Acad. Sci., USA, 72(11):4243-4247 (1975).

Heise et al., "ONYX-015, an E1B gene-attenuated adenovirus, causes tumor-specific cytolysis and antitumoral efficacy that can be augmented by standard chemotherapeutic agents," Nature Medicine, 3(6):639-645 (1997).

Henderson, S., "Induction of blc-2 Expression by Epstein Barr Virus Latent Membrane Protein 1 Protects Infected B Cells from Programmed Cell Death," Cell, 65:1107-1115 (1991).

Hollstein, M. et al., "p53 Mutations in Human Cancers," Science, 253: 49-53 (Jul. 1991).

Honess et al., "Proteins Specified by Herpes Simplex Virus XI. Identification and Relative Molar Rates of Synthesis of Structural and Nonstructural Herpes Virus Polypeptides in the Infected Cell", J. Virol., 12:1347-1365 (1973).

Houldsworth et al., "Human male germ cell tumor resistance to cisplatin is linked to TP53 gene mutation," Oncogene, 16:2345-2349 (1998).

Hubenthal-Voss et al., "Mapping of Functional and Antigenic Domains of the α4 Protein of Herpes Simplex Virus 1", J. Virol., 62:454-462 (1988).

Itoh et al., "The Polypeptide Encoded by the cDNA for Human Cell Surface Antigen Fas Can Mediate Apoptosis," Cell, 66:233-243 (1991).

Javier et al., "Genetic and Biological Analyses of a Herpes Simplex Virus Intertypic Recombinant Reduced Specifically for Neurovirulence", J. Virol., 61(6):1978-1984 (1987).

Johnson et al., "Why Do Neurons Die When Deprived of Trophic Factor?" Neurobiology of Aging, 10:549-552 (1989).

Katz et al., "Quantitative Polymerase Chain Reaction Analysis of Herpes Simplex Virus DNA in Ganglia of Mice Infected with Replication-Incompetent Mutants," J. Virology, 64(9):4288-4295 (1990).

Kauffman et al., "Pathogenesis of Viral Infections," in Fundamental Virology, Fields et al. (Eds.),Chapter 10, Raven Press, New York, pp. 153-167 (1986).

Kehm et al., "Restitution of the UL56 gene expression of HSV-1 HFEM led to restoration of virulent phenotype; deletion of the amino acids 217 to 234 of the UL56 protein abrogates the virulent phenotype," Virus Research, 40:17-40 (1996).

Kerbel, "What is the optimal rodent model for anti-tumor drug testing?", Cancer and Metastasis Rev. 17:301-304 (1999).

Kieff et al., "Size, Composition, and Structure of the Deoxyribonucleic Acid of Herpes Simplex Virus Subtypes 1 and 2", J. Virol., 8:125-132 (1971).

Kyte et al., "A Simple Method for Displaying the Hydropathic Character of a Protein," J. Mol. Biol., 157:105-132 (1982).

Larder et al., "Restoration of Wild-type Pathogenicity to an Attenuated DNA Polymerase Mutant of Herpes Simplex Virus Type 1", J. Gen. Virol., 67:2501-2506 (1986).

Linnemann et al., "Transmission of Herpes-Simplex Virus Type 1 in a Nursery for the Newborn Identification of Viral Isolates By D.N.A. "Fingerprinting" ", Lancet, 1:964-966 1978.

Loo et al., "Serial Passage of Embryonic Human Astrocytes in Serum-Free, Hormone-Supplemented Medium," J. Neuroscience Research, 28:101-109 (1991).

Lord et al., "Sequence of MyD116 CDNA: A novel myeloid differentiation primary response gene induced by IL6," Nucleic Acid Research, 18(9):2823 (1990).

Lowe, S.W. et al., "p53 Status and the Efficiency of Cancer Therapy in Vivo," Science, (Nov. 1994).

Mackem et al., "Structural Features of the Herpes Simplex Virus α Gene 4, 0, and 27 Promoter-Regulatory Sequences Which Confer α Regulation on Chimeric Thymidine Kinase Genes," J. Virology, 44(3):939-949 (1982).

Maclean et al., "Herpes simplex virus type 1 deletion variants 1714 and 1716 pinpoint neurovirulence-related sequences in Glasgow strain 17+ between immediate early gene 1 and the 'a' sequence", Journal of General Virology, 72(3):631-639 (1991).

MacLean et al., "The RL neurovirulence locus in herpes simplex virus type 2 strain HG52 plays no role in latency", J. Gen. Virol., 72:2305-2310 (1991).

Martuza, R.L. et al., "Experimental Therapy of Human Glioma by Means of a Genetically Engineered Virus Mutant," Science, 252:854-856 (May 1991).

McGeoch et al., "Complete DNA sequence of the short repeat region in the genome of herpes simplex virus type 1", Nucleic Acids Research, 14:1727-1745 (1986).

McGeoch et al., "The Complete DNA Sequence of the Long Unique Region in the Genome of Herpes Simplex Virus Type 1", J. Gen. Virol., 64:1531-1574 (1988).

McGoech et al., "Comparative sequence analysis of the long repeat regions and adjoining parts of the long unique regions in the genomes of herpes simplex viruses types 1 and 2", J. Gen. Virol., 72:3057-3075 (1991).

Meignier et al., "Construction and In Vivo Evaluation of Two Genetically Engineered Prototypes of Live Attenuated Herpes Simplex Virus Vaccines", Vaccines, 87, Cold Spring Harbor Laboratory, pp. 368-373 (1987).

Meignier et al., "In Vivo Behavior of Genetically Engineered Herpes Simplex Viruses R7017 and R7020. II. Studies in Immunocompetent and Immunosuppressed Owl Monkeys (*Aotus trivirgatus*)," J. Infectious Diseases, 162:313-321 (1990).

Meignier et al., "In Vivo Behavior of Genetically Engineered Herpes Simplex Viruses R7017 and R7020: Construction and Evaluation in Rodents", J. Infectious Diseases, 158: 602-614 (1988).

Meignier et al., "Virulence of and Establishment of Latency by Genetically Engineered Deletion Mutants of Hermes Simplex Virus 1", Virology, 162:251-254 (1988).

Mineta et al., "Treatment of Malignant Gliomas Using Ganciclovir-hypersensitive, Ribonucleotide Reductase-deficient Herpes Simplex Viral Mutant," Cancer Research, 54: 3963-3966 (1994).

Mocarski et al., "Site-specific inversion sequence of the herpes simplex virus genome: Domain and structural features", Proc. Natl. Acad. Sci., USA, 78:7047-7051 (1981).

Mocarski et al., "Structure and Role of the Herpes Simplex Virus DNA Termini in Inversion, Circularization and Generation of Virion DNA" Cell, 31:89-97 (1982).

Moriuchi et al., "Enhanced Tumor Cell Killing in the Presence of Ganciclovir by Herpes Simplex Virus Type 1 Vector-directed Coexpression of Human Tumor Necrosis Factor-α and Herpes Simplex Virus Thymidine Kinase," Cancer Research, 58:5731-5737 1998.

Morris Academic Press Dictionary of Science Technology Academic Press Harcourt Brace Jovanich Publishers, pp. 917 and 2276 (1992).

Morse et al., "Anatom of Herpes Simplex Virus (HSV) DNA", J. Virol., 26 2 389-410 (1978).

Muldoon et al., "Comparison of Intracerebral Inoculation and Osmotic Blood-Brain Barrier," American Journal of Pathology, 147(6):1840-1851 (1995).

Mulligan, R.C., "The Basic Science of Gene Therapy", Science, 260:926-930 (May 1993).

Nagata et al., "The Fas Death Factor," Science, 267:1449-1456 (1995).

Orkin et al., "Report and Recommendations of the Panel to Assess the NIH Investment in Research on Gene Therapy" (Dec. 1995).

Peppel et al., "A Simple and Fast Method to Extract RNA from Tissue Culture Cells," BioTechniques, 9(6):711-712 (1990).

Perry et al., "Characterization of the IE110 Gene of Herpes Simplex Virus Type 1", J. Gen. Virol., 67:2365-2380 (1986).

Perry et al., "The DNA Sequences of the Long Repeat Region and Adjoining Parts of the Long Unique Region in the Genome of Herpes Simplex Virus Type 1," J. Gen. Virol., 69:2831-2846 (1988).

Poffenberger et al., "A Noninverting Genome of a Viable Herpes Simplex Virus 1: Presence of Head-to-Tail Linkages in Packaged Genomes and Requirements for Circulation After Infection", J. Virol., 53(2):587-595 (1985).

Poffenberger et al., "Characterization of a viable, noninverting herpes simplex virus 1 genome derived by insertion and deletion of sequences at the junction of components L and S", Proc. Natl. Acad. Sci., USA, 80:2690-2694 (1983).

Post et al. "A Generalized Technique for Deletion of Specific Genes in Large Genomes: α Gene 22 of Herpes simplex Virus 1 is Not Essential for Growth", Cell, 25:227-232 (1981).

Post et al., "Cloning of reiterated and nonreiterated herpes simplex virus 1 sequences as BamHI fragments", Proc. Natl, Acad, Sci., USA, 77(7):4201-4205 (1980).

Ram et al., "Therapy of malignant brain tumors by intratumoral implantation of retroviral vector-producing cells," Nature Medicine, 3(12):1354-1361 (1997).

Rawson et al., "Death of Serum-free Mouse Embryo Cells Caused by Epidermal Growth Factor Deprivation," J. Cell Biology, 113:671-679 (1991).

Renfranz et al., "Region-Specific Differentiation of the Hippocampal Stem Cell Line HiB5 upon implantation into the Developing Mammalian Brain," Cell, 66:713-729 (1991).

Roizman et al., "The function of herpes simplex virus genes: A primer for genetic engineering of novel vectors," Proc. Natl. Acad. Sci. (USA) 93:11307-11312 (1996).

Roizman, B., in Fundamental Virology, Second Edition, Field et al.(Eds.) Chapters 5 and 33-34, Raven Press Ltd., New York (1991).

Roizman, B., in Virology, Second Edition, Field et al. (Eds.) Chapter 64, Raven Press Ltd., New York (1990).

Roller et al., "Herpes Simplex Virus 1 RNA-Binding Protein Us11 Negatively Regulates the Accumalation of a Truncated Viral mRNA," J. Virology, 65(11):5873-5879 (1991).

Ryder et al., "Establishment and Characterization of Multipotent Neural Cell Lines Using Retrovirus Vector-Mediated Oncogene Transfer", J. Neurobiol., 21:356-375 (1990).

Sanger et al., "DNA sequencing with chain-terminating inhibitors", Proc. Natl. Acad, Sci., USA, 74:5463-5467 (1977).

Sentman et al., "bcI-2 Inhibits Multiple Forms of Apoptosis but Not Negative Selection in Thermocytes," Cell, 67:879-888 (1991).

Sheldrick et al., "Inverted Repetitions in the Chromosome of Herpes Simplex Virus", Cold Spring Harbor Symp. Quant. Biol., 39:667-678 (1975).

Shih et al., "Expression of hepatitis B virus S gene by herpes simplex virus type 1 vectors carrying α- and β-regulated gene chimeras," Proc. Natl. Acad. Sci. (USA) 81:5867-5870 (1984).

Snyder et al., "Mulipotent Neural Cell Lines Can Engraft and Participate in Development of Mouse Cerebellum," Cell, 68:33-51 (1992).

Steller, H., "Mechanisms and Genes of Cellular Suicide," Science, 267:1445-1449 (1995).

Stevens et al., "Restriction of Herpes Simplex Virus by Macrophages", J. Exp. Medicine, 133:19-38 (1971).

Strasser et al., "bci-2 Transgene Inhibits T Cell Death and Perturbs Thymic Self-Censorship," Cell, 67:889-899 (1991).

Taha et al., "A Variant of Herpes Simplex Virus Type 2 Strain HG52 with a 1.5 kb Deletion in RL between 0 to 0.02 and 0.81 to 0.83 Map Units Is Non-neurovirulent for Mice", J. Gen. Virol., 70:705-716 (1989).

Taha et al., "The Herpes Simplex Virus Type 2 (HG52) Variant JH2604 Has a 1488 bp Deletion which Eliminates Neurovirulence in Mice", Journal of General Virology, 70(11):3073- 3078 (1989).

Thompson et al., "Biological Characterization of a Herpes Simplex Virus Intertypic Recombinant Which Is Completely and Specifically Non-Neurovirulent", Virology, 131:171-179 (1983).

Thompson et al., Functional and Molecular Analyses of the Avirulent Wild-Type Herpes Simplex Virus Type 1 Strain KOS, J. Virology, 58(1):203-211 (1986).

Thompson et al., "Herpes Simplex Virus Neurovirulence and Productive Infection of Neural Cells Is Associated with a Function Which Maps between 0.82 and 0.832 Map Units on the HSV Genome," Virolo, 172(2):435-450 (1989).

Thompson et al., "Physical Location of a Herpes Simplex Virus Type-1 Gene Function(s) Specifically Associated with a 10 Million-Fold Increase in HSV Neurovirulence", *Virology*, 131:180-192 (1983).

Thompson et al., "Rescue of a Herpes Simplex Virus Type 1 Neurovirulence Function with a Cloned DNA Fragment", *J. Virology*, 35(2):504-508 (1985).

Thompson et al., "Vaccine potential of a live avirulent herpes simplex virus," *Microbial Pathogenesis*, 1:409-416 (Aug. 1986).

Varmuza et al., "Signals for Site-Specific Cleavage of HSV DNA: Maturation Involves Two Separate Cleavage Events at Sites Distal to the Recognition Sequences", Cell, 41:793-802 (1985).

Verma et al., "Gene Therapy-Promises, Problems and Prospects," Nature 389:239-242 (1997).

Vlazny et al., "Site-specific cleavage/packaging of herpes simplex virus DNA and the selective maturation of nucleocapsids containing full-length viral DNA", Proc. Natl. Acad. Sci., USA, 79:1423-1427 (1982).

Wadsworth et al., "Anatomy of Herpes Simplex Virus DNA", J. Virol., 5(6):1487-1497 (1975).

Warren et al., "Isolation of Latent Herpes Simplex Virus from the Superior Cervical and Vagus Ganglions of Human Beings," New England Journal Medicine, 298:1068-1070 (1978).

Whitley, "Herpes Simplex Viruses", pp. 1843-1887 in Virology, Second Ed., Chapter 66 Fields et al., (eds.), Raven Press, New York (1990).

Whitley, R.J. et al., "Replication. Establishment of Latency, and Induced Reactivation of Herpes Simplex Virus γ1 34.5 Deletion Mutants in Rodent Models," J. Clin. Invest., 91:2387-2843 (Jun. 1993).

Williams, G.T., "Programmed Cell Death: Apoptosis and Oncogenesis," Cell 65:1097-1098 (1991).

TREATMENT OF TUMORS WITH GENETICALLY ENGINEERED HERPES VIRUS

STATEMENT OF GOVERNMENT INTEREST

This invention was made with government support under Grant Numbers CA047451, A1124009, CA001719, NS03096 and A1035871, awarded by the National Institutes of Health (NIH) and Grant Number De-FG05-93ER61654 awarded by the Department of Energy (DOE). The government has certain rights in the invention.

FIELD OF THE INVENTION

The present invention relates generally to use of modified Herpes simplex viruses as therapeutic treatment for tumors.

BACKGROUND OF THE INVENTION

The development of viruses as anticancer agents has been an intriguing yet elusive strategy. The goal of anticancer viral therapy is to inoculate a small percentage of tumor cells with replication competent viruses resulting in viral replication in the targeted tumor cells followed by cellular lysis (oncolysis) and infection of surrounding tumor cells. A key to viral oncolysis is genetic modification of the virus such that replication occurs principally in tumor cells and not in the surrounding normal tissue. Many strategies have focused on the use of genetically engineered viruses for oncolysis. For example, in one approach, attenuated retroviruses, modified to encode herpes simplex virus (HSV) thymidine kinase, were created to target dividing tumor cells [Culver, et al., Science 256: 1550-1552 (1992); Ram, et al. Nat. Med. 3:1354-1361 (1997)]. In this technique, however, viral infection of tumor cells was limited since only 10 to 15% of tumor cells were actively progressing through the cell cycle. In another approach, conditional replication-competent adenoviruses (E1b deleted) were designed to replicate only in tumor cells lacking p53, however only 50% of tumors are estimated to contain nonfunctional p53 [Bischoff, et al., Science 274: 373-376 (1996); Heise, et al. Nat. Med. 3:639-645 (1997); Hollstein, et al., Science 253: 49-53 (1991)]. The success of these strategies, therefore has been limited experimentally only to small tumor xenografts.

Recently, genetically engineered replication-competent HSV has been proposed to treat malignant gliomas [Martuza, et al., Science 252:854-856 (1991)]. In anti-glioma therapy, HSV-1 mutants were constructed to preferentially replicate in proliferating tumor cells thereby eliminating the risk of widespread dissemination of the virus in the central nervous system, which is observed in rare cases of HSV encephalitis in human. Initial strategies focused on deletion of viral genes encoding enzymes required for viral DNA synthesis (e.g., thymidine kinase, ribonucleotide reductase [Martuza, et al., Science 252:854-856 (1991); Mineta, et al., Cancer Res. 54: 3963-3966 (1994)]. More recent studies centered on the use of HSV mutants that lack a newly identified $\gamma_1 34.5$ gene involved in neurovirulence [Chou, et al., Science 250:1262-1266 (1990); Chou, et al., Proc. Natl. Acad. Sci. (USA) 89:3266-3270 (1992); Chou, et al., Proc. Natl. Acad. Sci. (USA) 92:10516-10520 (1995); Andreansky, et al. Cancer Res. 57:1502-1509 (1997)]. The combination of previous results suggested that a decrease in viral proliferative potential required for safe intracranial HSV inoculation, however, correlates with a decrease in the oncolytic potential of the virus [Advani, et al. Gene Ther. 5:160-165 (1998)]. The potential therapeutic effects of a genetically engineered HSV, having more potent antitumor efficacy than is possible for intracranial inoculation, has not been studied in models of common human tumors.

HSV offers many advantages as an oncolytic agent. The virus replicates well in a large variety on cancer cells and it destroys the cells in which it replicates. The virus can be attenuated by introducing specific deletions and it tolerates the insertion and expression of foreign genes [Meignier, et al., J. Infect. Dis. 158:602-614 (1988)]. Moreover, the functions of many HSV viral genes are known [Shih, et al., Proc. Natl. Acad. Sci. (USA) 81:5867-5870 (1984); Roizman, Proc. Natl. Acad. Sci. (USA) 93:113076-11312 (1996)]. The undesirable properties of HSV, however, include neuroinvasiveness, the ability to establish latency, and a capacity for reactivation from latent state.

Previous work has shown interactive effects of cytolytic capacity of modified HSV lacking both $\gamma_1 34.5$ genes and ionizing radiation on glioma xenografts [Advani, et al. Gene Ther. 5:160-165 (1998)]. Ionizing radiation combined with inoculation with $\gamma_1 34.5$-deficient HSV viruses resulted in supra-additive reduction in tumor xenograft volume and an enhancement in viral proliferation and intra-tumoral distribution in glioma xenografts.

R7020 is one such HSV strain attenuated by genetic engineering and tested in a variety of rodent, rabbit, and non-human primate models [Meignier, et al., J. Infect. Dis. 158: 602-614 (1988); Meignier, et al., J. Infect. Dis. 162:313-321 (1990)] which have shown that viral infectivity is attenuated in all species tested. A key property of interest in this strain is the lack of neuroinvasiveness even in the most susceptible species tested to date. R7020 is a modified HSV strain designed as a candidate for human immunization against HSV-1 and HSV-2 infections [Meignier, et al., Infect. Dis. 158: 602-614 (1988)]. Originally produced to be a live attenuated viral vaccine against HSV infection, R7020's has been examined for safety and stability in rodent and primate studies [Meignier, et al., J. Infect. Dis. 158: 602-614 (1988); Meignier, et al., J. Infect. Dis. 162:313-321 (1990)]. The construction of R7020 has been previously described [Meignier, et al., J. Infect. Dis. 158: 602-614 (1988); and Roizman, U.S. Pat. No. 4,859,587, incorporated herein by reference]. Briefly, wild-type HSV DNA consists of two regions of unique double-stranded DNA sequences flanked by inverted repeats [Roizman, et al., Proc Natl. Acad. Sci. (USA) 93:11307-11312 (1996)]. The inverted repeats regions contain two copies of five genes designated $\alpha 0$, $\alpha 4$, $\gamma_1 34.5$, ORF P and ORF O. R7020 contains an HSV-2 DNA fragment inserted in place of one set of the repeats and therefore lacks only one of the two copies of the $\gamma_1 34.5$ gene. Previously work has shown that, in certain cell lines, R7020 replicates more efficiently than viruses lacking both copies of the $\gamma_1 34.5$ gene [Advani, et al. Gene Ther. 5:160-165 (1998)]. To date, R7020 has been subjected to limited trials in humans.

One of the causes of failure in cancer therapy is tumor cell resistance to conventional cytotoxic and/or hormonal treatments that arises from genetic instability caused by these agents and inherent instability of tumor cells. For example, p53 gene deletion or mutation may decrease tumor cell susceptibility to apoptosis induced by chemotherapy and/or radiation [Houldsworth, et al., Oncogene 16:2345-2349 (1998); Aas. et al. Nat. Med. 2: 811-814 (1998); Lowe, et al., Science 266:807-810 (1994); Dalta, et al., Cell Growth Differ. 6:363-370 (1995)] and mutations in the androgen receptor lead to hormone resistance in prostate cancer. Also, "gain of function" mutations, such as activation of the bc1-2 family of genes, enhances resistance to a variety of cytotoxic therapies.

In addition to intrinsic genetic instability of tumor cells, commonly employed anticancer therapies that rely on DNA damage to tumor cells are mutagenic and a consequence of anticancer treatment is the selection and evolution of resistance to DNA damaging agents. One benefit of using viral lysis as an antitumor strategy is that viral lysis has the potential to overcome tumor resistance to conventional agents. Since tumor cell infection with replication component herpes results in cell lysis and is not per se mutagenic, selective evolution of tumor cells to evade herpes is less likely to occur within the tumor cell population.

Thus there exists a need in the art to identify and develop viral therapeutic agents and effective methods of treatment to retard and/or reduce tumor growth in patients in need thereof.

SUMMARY OF THE INVENTION

The present invention provides methods for treating cancer comprising the steps of administering to an individual in need thereof an effective amount of a Herpes simplex virus (HSV) comprising a modified HSV genome wherein said modification comprises a modification of an inverted repeat region of said HSV genome. In one embodiment, methods of the invention include use of HSV strains wherein the modification of the inverted repeat region of the genome comprises an alteration of a copy of a γ134.5 gene that renders that copy of the gene incapable of expressing an active gene product. In a preferred embodiment, methods of the invention comprise use of an HSV strain wherein the alteration of the $\gamma_1 34.5$ gene comprises (i) an insertion of a DNA sequence comprising one or more nucleotides into the coding region or regulatory region of the gene or (ii) a deletion of all or part of the coding region or regulatory region of the gene. Methods of the invention include use of HSV strains wherein the modified HSV genome further comprises an alteration in a unique region of the HSV genome.

Methods of the invention include treatment of noncentral nervous system cancer as well as central nervous system cancer.

DETAILED DESCRIPTION

The present invention provides materials and methods for treating a variety of tumors including noncentral nervous system tumors and tumors of the central nervous system origin. The treatment methods involve infecting target tumors with genetically modified herpes simplex virus wherein the modification comprises a modification of an internal inverted repeat region of the herpes simplex virus genome. In a preferred embodiment the modification of the herpes simplex virus genome comprises the deletion of one copy of the internal repeat sequence of the viral gene which region comprises one copy each of ICP0, IPC4, ORFO, ORFP and $\gamma_1 34.5$ genes. The herpes simplex viruses useful in the practice of the invention are attenuated with respect to the wild-type herpes simplex viruses but are more replication competent than viruses having both copies of the inverted repeat region modified (to render the region incapable of expressing an actual gene product of any one of the various genes) or deleted. Viruses useful in the practice of the present invention may have additional alterations in their genome that may include insertion of expressible non-natural protein encoding sequences under the control of herpes simplex virus promoters that in turn permits the sequence to be regulated as an α, β or γ class of herpes simplex virus genes that are well known in the art. [See, e.g. *Fundamental Virology, Second Edition*, Field et al. (eds.) Chapters 33-34, Raven Press Ltd., New York (1991) incorporated herein by reference.] Viruses lacking internal repeated can be further attenuated if necessary by the deletion of one or more of the 47 genes found dispensable for viral replication in, culture [Roizman, *Proc. Natl. Acad. Sci. (USA)* (1996)]. Among the genes suitable for deletion to decrease further virulence are the $U_L 16$, $U_L 40$, $U_L 41$, $U_L 55$, $U_L 56$, α22, $U_S 4$, $U_S 8$, and $U_S 11$ genes. Deletion of virtually any one of the "dispensable" genes will reduce virulence by a factor ranging from twofold to several logs. In addition, candidate viruses lacking the internal inverted repeats may be further altered by the addition of cytokines, as well as enzymes that activate prodrugs.

Herpes viruses useful in the practice of the invention may be prepared using methods well known in the art such as methods described in U.S. Pat. No. 4,859,587 (incorporated herein by reference.) and in U.S. Pat. No. 5,288,641 (also incorporated herein by reference.)

The examples set out below describe the use of herpes simplex virus type HSV-1 strain R7020 to reduce tumor size in mice. The use of mice as models for the treatment of tumorogenic disease is well known and widely accepted in the art. Example 1 describes the structure of HSV-1 strain R7020 which virus strain is illustrative of the kinds of genetically modified viruses that are useful in the practice of the present invention. Example 2 describes the use of a modified HSV-1 to reduce the tumor volume of a grafted epidermal carcinoma cell line in mice.

Example 3 describes the kinetics of viral replication in the epidermal carcinoma xenografts described in Example 1. The experiments described in Example 4 establish that epidermal carcinoma arising from residual tumor cells retain their susceptibility to infection by HSV-1 R7020.

The following examples are presented by way of illustration and are not intended to limit the scope of the invention as described in the appended claim.

EXAMPLE 1

Structure of HSV Strain R7020

The structure of R7020 (A.T.C.C. [American Type Culture Collection, 12301 Parklawn Drive, Rockville, Md. 20852] Accession No: VR2123, deposited Dec. 10, 1985), as described previously [Meignier, et al., *J. Infect. Dis.* 158:602-614 (1988)] includes an insertion comprising a HindIII fragment of HSV-2 DNA encompassing gene sequences encoding several glycoproteins inserted into the joint region of the parental HSV genome. A detailed analysis of the R7020 structure revealed differences from those reported by Meignier, et al. as described below.

First, insertion of the HSV-2 sequence leaves intact the parental HSV-1 $U_L 55$ gene whereas previous reports showed that part of the $U_L 55$ gene was deleted. The $U_L 55$ gene, however has no known function and probably does not affect safety of the virus. In addition, the $U_L 55$ region is preceded by 300 bp of "unknown sequence" at the joint region. As previously reported, the $U_L 56$ region that has been implicated in pathogenesis [Kehm, et al., *Virus Res* 40:17-40 (1996)] was not found in the corrected sequence.

Second, the $U_L 56$ sequences are duplicated at the joint region, which probably leads to defective genomes arising in a predictable and reproducible manner. Defective genomes are known to arise spontaneously in HSV-1 stocks if passaged at high multiplicity and defective genomes arise in R7020 more reproducibly and frequently. However, passage at low multiplicity of infection as is routine, minimizes the accumulation of defective genomes.

In another difference, only 5229 bp of the originally predicted 9629 bp of HSV-2 sequence were found in R7020.

EXAMPLE 2

Volumetric Reduction of Tumor Xenograft

In a first series of experiments, SQ-206 cells, a chemotherapy/radiation-resistant epidermal carcinoma cell line that expresses a nonfunctional p53, or PC-3 cells, a hormone-independent p53+ prostate adenocarcinoma cell line, were injected into the hind limb of nude mice. SQ-20b is an epidermal cancer cell line isolated from a patent following radiotherapy as described elsewhere [Hallahan, et al. *Nat. Med.* 1:786-791 (1995)]. PC-3 cell line was obtained from American Type Culture Collection (A.T.T.C. No. CRL 1435, Manassas, Va.). Large tumor xenografts were employed to approximate the relative mass of clinically evident, locally advanced human cancers. In contrast to earlier studies carried out with a tumor mass of approximately 100 mm$^3$, the experiments in this series were performed with tumors having a mean initial volume of 630 mm$^3$ corresponding roughly to 3% of mouse weight [Ram, et al. *Nat. Med.* 3:1354-1361 (1997)].

Briefly, SQ-20b tumor cells in amounts of 5×10$^5$ cells per mouse were suspended in 100 μl of sterile phosphate buffered saline (PBS), injected into the right hind limb of 5 to 6 week old athymic nu/nu mice, and grown to a tumor size of 200 to 1000 mm$^3$. The mouse hind limb model has been described elsewhere in detail [Advani, S. J. et al. Gene Ther. 5, 160-165 (1998)]. As previously reported, its major advantage is that it allows the measurement of the effects on oncolytic agents without recourse to invasive procedures. The previously described model was modified to increase the mean size of the xenograft from 100 to 600 mm$^3$ at the time treatment by virus injection was initiated, to increase the ratio of cells to virus and approximate more closely the size of the tumor in clinically relevant situations.

Mice were randomized into two treatment groups: (a) controls administered 10 μl of a buffer solution and (b) mice administered 2×10$^6$ plaque forming units (pfu) of R7020 in 10 μl of buffer with a Hamilton syringe. The genetically engineered R7020 virus is derived from HSV-1(F) which is the prototype HSV-1 virus [Meignier, et al., supra]. R7020 lacks $U_L24$, $U_L56$, and one set of the inverted repeats encoding one copy of the genes α0, α4, $γ_1$34.5, ORFP and ORFO. The deleted region of the internal inverted repeat of HSV-1(F) was replaced by a DNA fragment encoding HSV-2 glycoproteins G, J, D, and I [Meignier, et al., *J. Infect. Dis.* 158:602-614 (1988)]. Virus was titered on Vero cells (American Type Culture Collection, Manassas, Va.) as described elsewhere [Chou, et al., *Science* 250:1262-1266 (1990)]. The tumor mass was measured biweekly or until tumor volume reached 2000 mm$^3$. Tumor volumes were calculated using the formula (length×width×height)/2 which is derived from the formula of an elipsoid (δd$^3$)/6. Animal studies were performed according to a protocol approved by the Animal Resource Center at the University of Chicago. Fraction tumor volume was defined as tumor volume at the specific time point divided by the initial volume (V/V$_0$). Animals were sacrificed when tumor volume exceeded 2000 mm$^3$. Similar experiments were carried out with PC-3, with the only exception that 2×10$^7$ cells in 100 μl of PBS were injected per xenograft.

Result indicated that SQ-20b xenografts treated with R7020 began to regress 13 days after infection and reached a nadir at 41 days post-infection at which time the mean tumor volume reduction was down to one fifth of the initial tumor volume. Seventy two percent (8 of 11) of the tumor xenografts regressed to less than 10% of the initial tumor volume by day 41, and 7 of these 8 retained the reduced size for greater than 80 days.

R7020 was effective in tumor volume regression of PC-3 prostate adenocarcinoma xenografts as well. Fractional tumor volume achieved a nadir approximately 20 to 30 days after infection. R7020 was also as effective in causing regression of a hepatoma adenocarcinoma tumor xenograft.

EXAMPLE 3

Kinetics of Viral Replication in SQ-208 Xenografts

In order to assess the kinetics of viral replication in the SQ-208 xenografts, the following procedures were carried out. SQ20 xenografts were injected with 2×10$^6$ pfu of R7020 or with buffered saline. The mice injected with virus were divided into two groups. One group was sacrificed at specified times. Tumors were aseptically harvested at specific time points after infection, snap frozen in liquid nitrogen, and stored at −70° C. Tumors were homogenized in 1 ml of 199V and 1 ml of sterile skim milk for 20 seconds on ice using a Polytron tissue homogenizer (Kinematics, Switzerland). The homogenate was sonicated three times for 15 seconds each and virus was titered on Vero cells.

The tumor volumes in mice injected with saline and those of the second group of identically treated mice injected with virus were tested for tumor volume. As in the experiment described in Example 2, tumors injected with buffered saline grew exponentially whereas tumors injected with virus regressed. Viral titers peaked at seven days after infection with 124×10$^5$ pfu/tumor, i.e., a 62-fold increase in virus over the amount injected into the tumors. Significant amounts of virus (greater than 10$^5$ pfu) were recovered at late as 30 days after infection.

EXAMPLE 4

Tumor cells Resistance to Oncolytic Effects of R7020

In order to assess the ability of SQ-20b tumor cells to become resistant to the oncolytic effects of R7020, the following experiments were performed.

Tumors were grown as described above. When tumors were greater than 200 mm$^3$, they were injected with 2×10$^6$ pfu of R7020 in 10 μl of buffer on day 0. Tumors were measured biweekly. As tumors regrew to their starting tumor volume (volume at day 0), they were randomized and re-injected with either 10 μl of buffer, 2×10$^6$ pfu of R7020, or 2×10$^6$ pfu of HSV-1(F) in the same volume of buffer. Animals with tumor volume greater than 200 mm$^3$ were sacrificed following institutional guidelines.

Results indicated that all three buffer re-injected tumors continued to increase the size. Fractional tumor volume decreased following the second viral injection of either R7020 or HSV-1(F). Tumors continued to show sensitivity for viral oncolysis through two cycles of R7020 injection and did not recur for at least 120 days from the initiation of the experiment. Mice reinjected with HSV-1(F) died four to six weeks following wild-type virus injection whereas mice reinjected with R7020 thrived. Thus, SQ-20b tumors arising from residual cells in tumors previously treated with R7020 retain susceptibility to infection.

EXAMPLE 5

R7020 Treatment in Combination with Irradiation

Earlier studies on glioma xenografts have shown that the combination of irradiation and administration of an attenuated HSV result in enhanced tumor cell destruction as well as enhanced viral replication [Advani, et al. *Gene Ther.* 5:160-165 (1998)]. To determine whether irradiation of the radiation-resistant SQ-206 cell lines enhanced the oncolytic effect of R7020, xenografts were infected as described above and subjected to a fractionated irradiation protocol as described below.

Irradiation of xenografts was carried out as described elsewhere [Advani, et al. *Gene Ther.* 5:160-165 (1998)]. Briefly, tumor-bearing hind limbs were exposed to ionizing radiation using a GE 250 kv maxitron generator (191 cGy/min, 150 kVp). Irradiation was administered starting six hours after infection with R7020 in 400 cGy fractions on Monday, Tuesday, Thursday, and Friday for two weeks up to a maximum dosage of 3200 cGy. Fractionated irradiation was administered in doses routinely employed in clinically relevant protocols.

Results indicate that irradiation alone resulted in a modest delay in xenograft growth compared to control tumors confirming radiation resistance of the SQ-206 cell line. While tumor volume reduction did not occur until 13 days after infection of xenografts with R7020 as described in Example 2, combining irradiation with R7020 resulted in tumor volume regression one week earlier than tumors treated with R7020 alone. In addition, the nadir in tumor volume occurred significantly earlier in xenografts receiving both irradiation and R7020 as compared to xenografts receiving R7020 alone (day 20 versus day 30).

These results demonstrate for the first time dramatic antitumor efficacy of R7020 in the treatment of experimental human tumors frequently resistant to common cancer treatments and suggest that, while R7020 is an effective antitumor agent by itself, combining irradiation with R7020 also provides more rapid and complete tumor cell destruction. The combination of irradiation and attenuated HSV as an anticancer therapy may prove to be especially beneficial in clinical situations where the tumor burden may be too large for single agent therapy.

Numerous modifications and variations in the invention as set forth in the above illustrative examples are expected to occur to those skilled in the art. Consequently only such limitations as appear in the appended claims should be placed on the invention. References cited herein are incorporated by reference in their entireties.

What is claimed is:

1. A method for reducing a non-central nervous system tumor mass comprising the step of administering to an individual suffering from cancer an amount of a Herpes simplex virus (HSV) comprising a modified HSV genome wherein said modification comprises a modification of an inverted repeat region of said HSV genome such that one $\gamma_1 34.5$ gene remains intact, wherein said HSV is HSV R7020, said amount of HSV being effective to reduce the non-central nervous system tumor mass and being safe for administration to the patient.

2. The method of claim 1 wherein the modification of the inverted repeat region of the genome comprises an alteration of a copy of a $\gamma_1 34.5$ gene which renders that copy of the gene incapable of expressing an active gene product.

3. The method of claim 2 wherein the alteration of the $\gamma_1 34.5$ gene comprises an insertion of a DNA sequence comprising one or more nucleotides into the coding region or regulatory region of the gene.

4. The method of claim 2 wherein the alteration of the $\gamma_1 34.5$ gene comprises a deletion of all or part of the coding region or regulatory region of the gene.

5. The method of claim 1 wherein the modified HSV genome further comprises an alteration in a unique region of the HSV genome.

6. The method of claim 5 wherein the unique region comprises a gene selected from the group consisting of $U_L 16$, $U_L 40$, $U_L 41$, $U_L 55$, $\alpha 22$, $U_s 4$, $U_s 8$, and $U_s 11$.

7. The method of claim 1 wherein the modified HSV is administered to the tumor mass by direct injection.

8. The method of claim 1, wherein the non-central nervous system tumor mass is an epidermal carcinoma.

9. The method of claim 1, wherein the non-central nervous system tumor mass is a prostate adenocarcinoma.

10. The method of claim 1, wherein the non-central nervous system tumor mass is a hepatoma adenocarcinoma.

11. The method of claim 1, wherein the HSV is administered in combination with radiation.

12. The method of claim 1, wherein the HSV is administered in the absence of radiation.

13. A method for treating a patient with a radiation-resistant epidermal tumor mass comprising administering to a patient suffering from the radiation-resistant tumor mass a therapeutically effective amount of HSV R7020, wherein said administering results in one or more tumor cells infected with said HSV, said amount of HSV being effective to reduce the non-central nervous system tumor mass and safe for administration to the patient.

14. The method of claim 13, wherein the HSV is administered in combination with radiation.

15. The method of claim 13 wherein the modified HSV genome is a HSV having the genotype of the virus deposited under American Type Culture Collection (A.T.C.C.) Accession Number VR2123.

16. The method of claim 1 wherein the modified HSV genome is a HSV having the genotype of the virus deposited under American Type Culture Collection (A.T.C.C.) Accession Number VR2123.

* * * * *